United States Patent [19]

Thompson et al.

[11] Patent Number: 4,866,186

[45] Date of Patent: Sep. 12, 1989

[54] PROCESS FOR THE FORMATION OF 6-DESMETHYL-6-EXO-METHYLENE DERIVATIVES OF LOVASTATIN AND ANALOGS THEREOF

[75] Inventors: Andrew S. Thompson, Mountainside; Thomas R. Verhoeven, Cranford; Ichiro Shinkai, Westfield, all of N.J.

[73] Assignee: Merck & Co., Inc., Rahway, N.J.

[21] Appl. No.: 213,870

[22] Filed: Jun. 30, 1988

[51] Int. Cl.$^4$ .......................................... C07D 309/30
[52] U.S. Cl. .................................................... 549/292
[58] Field of Search ........................ 549/292; 514/460

[56] References Cited

PUBLICATIONS

P. A. Grieco, J. Org. Chem. 41, 1485 (1976).

Primary Examiner—Glennon H. Hollrah
Assistant Examiner—Susan P. Treanor
Attorney, Agent, or Firm—Melvin Winokur; Joseph F. DiPrima

[57] ABSTRACT

A process and intermediates in preparation of 6-exomethylene derivatives of lovastatin and 8-acyl and di- and tetrahydro analogs thereof is disclosed.

3 Claims, No Drawings

PROCESS FOR THE FORMATION OF 6-DESMETHYL-6-EXO-METHYLENE DERIVATIVES OF LOVASTATIN AND ANALOGS THEREOF

BACKGROUND OF THE INVENTION

Hypercholesterolemia is known to be one of the prime risk factors for ischemic cardiovascular disease, such as arteriosclerosis. Bile acid sequestrants have been used to treat this condition; they seem to be moderately effective but they must be consumed in large quantities, i.e. several grams at a time and they are not very palatable.

MEVACOR ® (lovastatin), now commercially available, is one of a group of very active antihypercholesterolemic agents that function by limiting cholesterol biosynthesis by inhibiting the enzyme, HMG-CoA reductase. In addition to the natural fermentation products, mevastatin and lovastatin, there are a variety of semi synthetic and totally synthetic analogs thereof.

The naturally occurring compounds and their semi-synthetic analogs have the following general structural formulae:

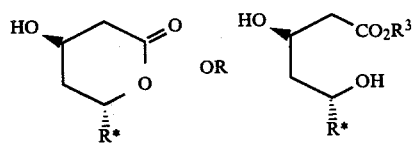

wherein:

$R^3$ is hydrogen, $C_{1-5}$ alkyl or $C_{1-5}$ alkyl substituted with a member of the group consisting of phenyl, dimethylamino, or acetylamino; and $R^*$ is

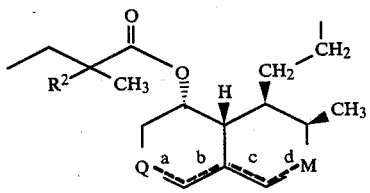

wherein Q is

or $R^5$-CH; $R^5$ is H or OH; M is

$R^6$ is hydrogen or hydroxy;

$R^2$ is hydrogen or methyl; and a, b, c, and d represent single bonds, one of a, b, c or d represents a double bond, or both a and c or both b and d represent double bonds provided that when a is a double bond, Q is

or

and when d is a double bond, M is

Active metabolites of lovastatin which possess a 2,3,5,6,7,8-hexahydronapthyl moiety and a 3-hydroxy group are disclosed and claimed in co-pending application Ser. No. 856,251, filed Apr. 28, 1986. These metabolites are represented by the following general structural formulae:

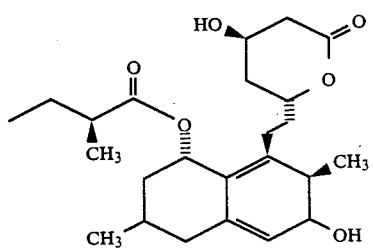

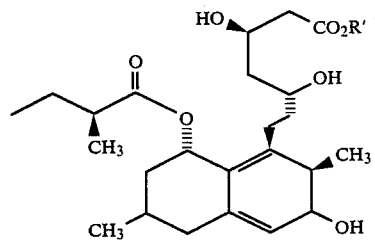

Copending application Ser. No. 067,503, filed June 29, 1987 discloses and claims active metabolites of lovastatin which possess a 6-exomethylene moiety. These metabolites are represented by the following structural formulae:

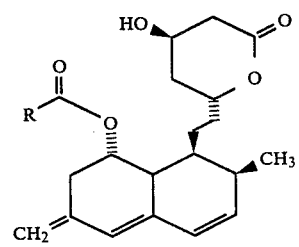

-continued

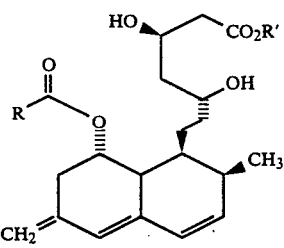

wherein:

R is $C_{1-10}$ alkyl:

R' is hydrogen, $C_{1-5}$alkyl, or $C_{1-5}$ alkyl substituted with a member of the group consisting of phenyl, dimethylamino, or acetylamino.

It would be very useful to be able to prepare such 6-exomethylene derivatives in a synthetic scheme from available starting materials.

DETAILED DESCRIPTION OF THE INVENTION

This invention relates to novel intermediates, and a novel process for their preparation where said intermediates are useful in a novel preparation of 6-exomethylene derivatives of lovastatin and 8-acyl and di and tetrahydro analogs thereof. Said 6-exomethylene derivatives of lovastatin and 8-acyl analogs thereof are useful in treating hypercholesterolemia and are disclosed in copending application Ser. No. 067,503 filed June 29, 1987.

The overall process of this invention for preparing the 6 exomethylene derivatives of lovastatin is shown in Scheme 1.

In the present invention the hydroxyl group on the 6 hydroxylmethyl moiety is selectively converted into a phenyl selenide or sulfide which is then oxidized and eliminated to yield the 6-exomethylene derivative. The instant process discriminates between the two hydroxyl groups resident in the starting material. Although the product (III) of the reaction, particularly when a and b are both double bonds, would be expected to be highly liable to acid conditions and aromatization, the present method produces product (III) with a purity $\geq 97\%$. Furthermore the conditions of the present process are such that the selenenic moieties involved do not react with the a and/or b sites, although phenyl selenenyl halides are known to react when both a and b are double bonds.

SCHEME 1

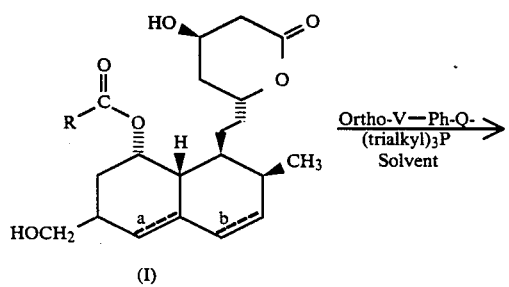

-continued

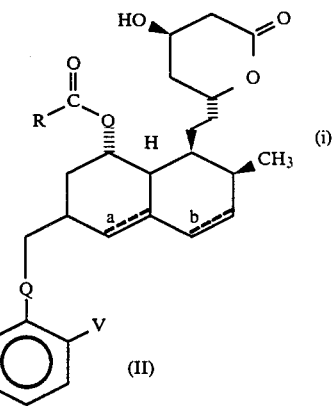

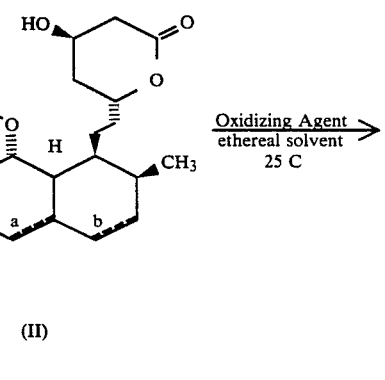

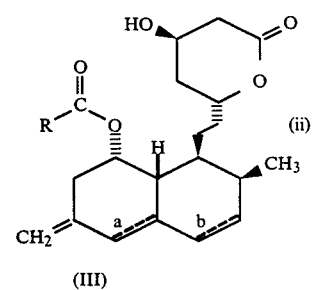

R = $C_{1-10}$alkyl;
Q = Se or S;
V = H or $NO_2$;
a and b are double or single bonds.

The intermediates (II) of the present invention are prepared in a novel process (i) which comprises: treating the starting material (I)

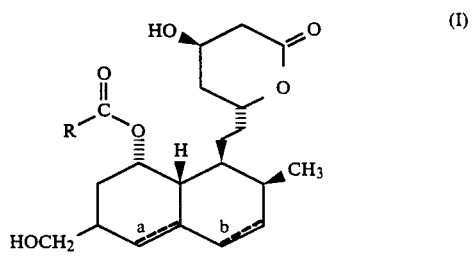

wherein:

R is $C_{1-10}$alkyl and a and b are double bonds or one of a and b is a single bond or both a and b are single bonds; with a trialkylphosphine such as tri-n butylphosphine or hexamethylphosphoric triamide (HMPT) and a reagent for forming a phenyl selenide or a phenyl sulfide such as a phenyl selenocyanate, such as O-nitrophenylselenocyanate or a N-phenyl selenoimide such as N-phenyl selenophthalimide or N phenyl seleno succimide or the N-phenyl sulfurimide analog or diphenyl disulfide, in a halogenated solvent such as methylene chloride or an ethereal solvent such as tetrahydrofuran or a hydrocarbon solvent such as hexane or benzene.

Intermediates (II) are used to form products (III) in a process (ii) which comprises: contacting intermediate (II), dissolved in an ethereal solvent such as tetrahydrofuran or a hydrocarbon solvent such as hexane or benzene, with an oxidizing agent such as 30% hydrogen peroxide or peroxybenzoic acid or t-butylhydroperoxide, at 25°–35° C.

It should be understood that the $C_{1-10}$ alkyl group of this invention may either be in a straight chain or branched configuration.

One embodiment of this invention is the compounds of formula (II):

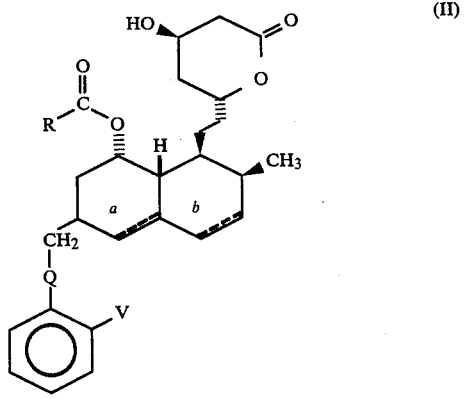

wherein Q is Se or S, V is H or $NO_2$, and R, a and b are defined above. In one class of this embodiment R is sec butyl or 1,1-dimethylpropyl, V is $NO_2$ and a and b are double bonds.

Exemplifying this embodiment is 6(R)-[2-[8(S)-(2,2-dimethylbutyryloxy)-2(S)-methyl-6-(2-nitrophenylselenylmethyl) 1,2,7,8,8a(R)-pentahydronaphthyl-1(S)]ethyl]-4(R)-hydroxy-3,4,5,6-tetrahydro-2H-pyran-2-one.

A second embodiment of this invention is the process (i) for the preparation of intermediates (II) from starting material (I). This process consists of treating (I) with a trialkylphosphine such as tri-n-butylphosphine or with hexamethylphosphoric triamide (HMPT) preferably tri n-butylphosphine and a reagent for forming a phenyl selenide or a phenyl sulfide such as a phenyl selenocyanate such as o-nitrophenylselenocyanate or an N-phenyl selenoimide such as N-phenyl selenophthalimide or N phenyl selenosuccimide or the N phenyl sulfurimide analog or diphenyl disulfide, preferably a phenyl selenocyanate most preferably o- nitrophenyl selenocyanate, in a halogenated hydrocarbon such as methylene chloride or an ethereal solvent such as tetrahydrofuran or a hydrocarbon solvent such as hexane or benzene preferably methylene chloride, at about 20° C.

Starting material (I) is dried by distilling off a toluene azeotrope followed by high vacuum drying. The dried alcohol (I) is dissolved in a solvent, preferably methylene chloride, and a trialkylphosphine, preferably tri-n-butylphosphine, is added in approximately a 4:3 mole ratio to starting alcohol. A solution of a phenyl-selenocyanate or other reagent for forming a phenylselenide or phenylsulfide in a solvent, preferably methylene chloride, is added dropwise to the alcohol/phosphine mixture. The mole ratio of added selenocyanate to alcohol is approximately 4:3. The reaction mixture was stirred at ambient temperature for about 3 hours and solvent and HCN gaseous byproduct removed in vacuo. The mixture was then worked up by standard procedures to yield intermediate (II).

Intermediate (II), dissolved in an ethereal solvent or a hydrocarbon solvent, preferably an ethereal solvent, most preferably tetrahydrofuran, is treated with an oxidizing agent such as 30% hydrogen peroxide, peroxybenzoic acid or t-butylhydroperoxide or the like, preferably hydrogen peroxide. The reaction mixture is brought between 25°–35° C. and stirred for about 45 minutes. When the temperature begins to rise, the reactant composition is stirred for an additional 5–10 minutes and then quenched with an alkaline ice cold mixture such as saturated $NaHCO_3$. The reaction mixture is then worked up by standard procedures to yield product (III).

Starting compounds (I), wherein a and b are double bonds are conveniently prepared from lovastatin, or its analogs having a 6- methyl group, employing a cultivation of a microorganism of the genus Nocardia, following the procedures in copending application 048,136 filed May 15, 1987 which procedures are hereby incorporated by reference.

Starting compounds (I) wherein a and/or b are single bonds are prepared from lovastatin, or its analogs having a 6-methyl group, employing a synthetic procedure described in copending application 048,136 filed May 15, 1987 which procedure is hereby incorporated by reference.

Compounds wherein R is other than sec-butyl are conveniently prepared from lovastatin by hydrolysis of the acyl moiety and reesterification following the procedure in U.S. Pat. No. 4,444,784.

The phenylselenium reagents are commercially available or the preparation can be accomplished by standard chemical transformations (see e.g. Grieco et al., *J. Org. Chem.* 41, 1485 (1976) and *J. Org. Chem.* 46, 1215 (1981)). The phenylsulfur reagents can be prepared as described in Walker, Tetrahedron Letters, 4475 (1977).

The following examples illustrate the present invention and as such are not to be considered as limiting the invention set forth in the claims appended hereto.

EXAMPLE 1

Preparation of 6(R)-[2-[8(S)-(2,2-dimethylbutyryloxy)-2(S)-methyl-6-exomethylene-1,2,7,8,8a(R)-pentahydronaphthyl-1(S)]ethyl-4-(R)-hydroxy-3,4,5,6,-tetrahydro-2H-pyran-2-one (a): 6(R)-[2-[8(S)-(2,2-dimethylbutyryloxy)-2(S)-methyl-6(S)-(ortho nitrophenylselenylmethyl)-1,2,6,7,8,8a(R) hexahydronaphthyl-1 (S)]ethyl]-4-(R)-hydroxy-3,4,5,6-tetrahydro-2H-pyran-2-one (1a)

In a dry 100 mL pear shaped flask was placed o-nitrophenyl selenocyanate (9.5 g, 41.8 mmol) and dry $CH_2Cl_2$ (20 mL).

In a separate flask was placed 6(R)-[2-[8(S)-(2,2-dimethylbutyryloxy)-2(S)-methyl-6(S)-hydroxymethyl-1,2,6,7,8,8a(R)-hexahydronaphthyl-1(S)]ethyl-4(R)-hydroxy-3,4,5,6,-tetrahydro-2H-pyran-2-one (14.4 g, 33.3 mmol) which was dried via a toluene azeotrope on a rotovap (2×40 mL) followed by high vacuum drying (0.5 mm/1 hour) just prior to use. To the above alcohol under $N_2$ was added dry $CH_2Cl_2$ (80 mL), and tri-n butylphosphine (10.2 mL, 41.0 mmol). The methylene chloride solution of selenocyanate prepared as outlined above was transferred via syringe to a dropping funnel and added dropwise over about 5 minutes to the alcohol/phosphine mixture.

Additional methylene chloride (10 ml) was added to the flask which contained the selenocyanate and any remaining selenocyanate was dissolved and transferred via syringe to a dropping funnel and then added dropwise to the alcohol/phosphine mixture. This procedure was repeated 3 times.

The dark red reaction mixture was stirred at ambient temperature for 2.5 hours and then the methylene chloride and HCN (byproduct) were removed in vacuo. The residue was dissolved in 500 mL of hexane:ethyl acetate (1:1) and washed with $H_2O$ (3×150 mL). The combined aqueous layers were washed with hexane:ethyl acetate (150 mL). The combined organic layers were washed with brine, dried ($Na_2SO_4$) and concentrated.

The resulting red oil was purified by silica gel flash chromatography (gradient elution using 3:1, 2:1, 1 5:1, 1:1 hexane:ethyl acetate containing 2% methanol) to afford compound (1a) as a yellow foam Rf of Compound (1a) is 0.51 [silica gel using chloroform:methanol 10:1 (v/v)]; 1H NMR (300 MHz,CDCl$_3$) 8.28(d,J=8.1 Hz,1H), 7.50(m,2H,Ar-H), 7.32(m,1H,Ar H), 5.99(d,J=9.7 Hz,1H,H-4), 5.83(dd,J=9.7,5.9 Hz,1H,H-3), 5.58(s,1H,H-5), 5.35(s,1H,H-8), 4.62 (m,1H,H-2'), 4.38(m,1H,H-4'), 2.98(AB of an ABX, J=11.5,6.8 Hz,1H,ArSeCH), 2.94(AB of an ABX, J=11.5,6.8 Hz,1H,ArSeCH), 2.74(dd,J=17.6,5.0 Hz, 1H,H-5'), 2.65(m,2H), 2.38(m,3H), 2.05–1.80(m,3H), 1.75–1.20(m,8H), 1.09(s,3H), 1.07(s,3H), 0.92(d,J=7.0 Hz,3H), 0.75(t,J=7.4 Hz,3H).

(b): 6(R)-[2-[8-(S)-(2,2-dimethylbutyryloxy)-2(S)-methyl-6-exomethylene-1,2,7,8,8a pentahydronaphthyl-1(S)]ethyl-4(R)-hydroxy-3,4,5,6,-tetrahydro-2H -pyran-2-one. (1b)

Selenide (1a) (0.5 g, 0.81 mmol) was dissolved in THF (5 mL) followed by the addition of $H_2O_2$ (30%, 0.5 mL, 5.8 mmol). The mixture was heated in a warm water bath to 25° C. (internal temperature). In 30–45 minutes the internal temperature began to rise above the temperature of the water bath. The reaction was stirred an additional 5–10 minutes and quenched with ice-cold saturated $NaHCO_3$.

The reaction was diluted with ethyl acetate (20 mL) and the organic layer separated. The aqueous layer was extracted with ethyl acetate (2×20 mL) and the combined organic layers washed with saturated $NaHCO_3$, brine, dried ($Na_2SO_4$) and concentrated to afford the 6 exomethylene as an orange oil. Analysis by 300 MHz 1H NMR showed <5% of any impurities. The orange color of this material could be removed by rapid filtration through a plug of silica gel eluting with 2:1 then 1:1 hexane:ethyl acetate (containing 2% MeOH and 2% Et3N). Fractions were collected when eluting with the more polar solvent. This afforded the triene as an off white foam. $^1$H NMR (300 MHz,C$_6$D$_6$) 6.03(m,2H,H-4 and H-5), 5.80(dd,J=9.50,6.10 Hz,1H,H-3), 5.25(d,J=2.6 Hz,1H,H 8), 4.90(s,1H,C=CH$_2$), 4.70(s,1H,C=CH$_2$), 4.60(m,1H,H-2'), 3.86(app. t,J=3.8 Hz,1H,H-4), 3.0(br s,1H,OH), 2.80(dd,J=16.1,3.4 Hz,1H,H-7), 2.52(d,J=17.5 Hz,1H), 2.38(d,J=4.7 Hz,1H), 2.35 2.10(m,3H), 1.80 1.00(m,9H), 1.12(s,3H), 1 11(s,3H), 0.83(d,J=7.4 Hz,3H), 0.79(t,J=7.1 Hz,3H); $^{13}$C NMR (75 MHz,C$_6$D$_6$) 177.55, 170.05, 140.31, 136.21, 135.84, 128.54, 126.17, 113.09, 76.04, 67.92, 62.69, 43.24, 39.07, 38.19, 37.30, 35.94, 35.38, 33.38, 31.47, 25.19, 24.77, 24.26, 13.63, 9.63; UV(MeOH) max=283,272,262 nm.

What is claimed is:

1. A compound of structural formula (II):

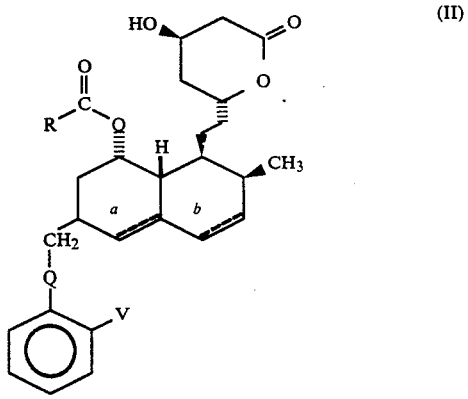

(II)

wherein:

R is $C_{1-10}$ alkyl; and a and b are both double bonds, or one of a and b is a single bond, or both a and b are single bonds; and Q is Se or S and V is H or $NO_2$.

2. A compound of claim 1 wherein: R is sec butyl or 1,1-dimethylpropyl; and a and b are double bonds; and Q is Se and V is $NO_2$.

3. A compound of claim 2 wherein R is 1,1-dimethylpropyl.

* * * * *